US007824380B2

(12) United States Patent
Iijima et al.

(10) Patent No.: US 7,824,380 B2
(45) Date of Patent: Nov. 2, 2010

(54) METHOD FOR MOUNTING A GASKET ON A PLUNGER

(75) Inventors: Kazumi Iijima, Gunma (JP); Kazuyuki Yanase, Fukaya (JP)

(73) Assignees: Bracco International B.V., Amsterdam (NL); Daikyo Seiko, Ltd., Tokyo (JP)

( * ) Notice: Subject to any disclaimer, the term of this patent is extended or adjusted under 35 U.S.C. 154(b) by 0 days.

(21) Appl. No.: 11/976,245

(22) Filed: Oct. 23, 2007

(65) Prior Publication Data

US 2008/0051728 A1    Feb. 28, 2008

Related U.S. Application Data

(62) Division of application No. 10/030,711, filed as application No. PCT/JP00/04754 on Jul. 14, 2000, now abandoned.

(30) Foreign Application Priority Data

Jul. 15, 1999   (JP) ................. 11-201814

(51) Int. Cl.
*A61M 5/315* (2006.01)
(52) U.S. Cl. ..................................... 604/218
(58) Field of Classification Search ......... 604/181, 604/187, 212–230
See application file for complete search history.

(56) References Cited

U.S. PATENT DOCUMENTS

| 3,828,980 | A | 8/1974 | Creighton et al. |
| 4,718,463 | A | 1/1988 | Jurgens, Jr. et al. |
| 4,961,728 | A | 10/1990 | Kosinski |
| 5,460,617 | A | * | 10/1995 | Minkus et al. ............ 604/218 |
| 5,685,864 | A | 11/1997 | Shanley et al. |
| 5,688,252 | A | 11/1997 | Matsuda et al. |
| 5,752,940 | A | 5/1998 | Grimard et al. |
| 6,042,565 | A | 3/2000 | Hirschman et al. |
| 6,068,614 | A | * | 5/2000 | Kimber et al. ............ 604/200 |
| 6,331,173 | B1 | 12/2001 | Ljungquist et al. |

FOREIGN PATENT DOCUMENTS

| JP | 06-327771 | 11/1994 |
| JP | 08-052214 A | 2/1996 |
| JP | 09-308689 | 12/1997 |
| JP | 10-000212 U | 9/1998 |
| WO | WO-96/14100 | 5/1996 |
| WO | WO-98/17336 | 4/1998 |

OTHER PUBLICATIONS

JPO Notification of Reason for Refusal, App. No. 2001-510541, Dispatch No. 096115, Dispatch Date: Feb. 26, 2008 (4 pages).
Communication pursuant to Article 96(2) EPC from the European Patent Office.

* cited by examiner

*Primary Examiner*—Matthew F Desanto
(74) *Attorney, Agent, or Firm*—Rader, Fishman & Grauer PLLC

(57) ABSTRACT

A gasket 7 used for a prefilled syringe 1 in which liquid 3 is filled, having a constriction 8 on its circumferential side face in contact with an inner surface of a syringe barrel 2 and having a bottom face 7c which is not in contact with the liquid 3 whose circumference is formed in a tapered shape.

2 Claims, 6 Drawing Sheets

METHOD FOR MOUNTING A GASKET ON A PLUNGER

CROSS REFERENCE TO RELATED APPLICATIONS

The present application is a Divisional Application of patent application Ser. No.: 10/030,711, filed Apr. 22, 2002, which is a national stage application of PCT/JP00/004754 filed Jul. 14, 2000, which claims priority to Japanese Patent Application JP 11-201814 filed on Jul. 15, 1999, the entire contents of which are herein incorporated by reference.

TECHNICAL FIELD

The present invention relates to a plunger for a syringe used for supporting and moving a gasket inserted in a syringe barrel.

BACKGROUND ART

In a general syringe, a liquid medicine is inhaled into its syringe barrel when it is used, but recently a prefilled syringe in which the liquid medicine is previously filled in the syringe barrel was developed to reduce a working load at a medical site. A prefilled syringe in which a contrast medium is filled in its syringe barrel has also come into use lately. Moreover, a prefilled plastic syringe in which a contrast medium is previously filled in its plastic syringe having comparatively large capacity is also used these days.

When such a syringe is used, a plunger is inserted from a rear end of the syringe barrel and a screw portion formed at a tip of the plunger is screwed in a rear face of a gasket so that the gasket is mounted at the tip of the plunger. The gasket is thus mounted at the tip of the plunger and the gasket is pushed via the plunger, which causes the liquid medicine to be injected into a body or the like. Further, since the contrast medium has comparatively high viscosity and resistance when the contrast medium is injected into the body via a blood-vessel, spinal cord, or the like is large, pressure injection is generally performed using a device such as an auto-injector in a case of using the syringe in which the contrast medium is filled.

When the gasket is mounted at the tip of the plunger in this way, if a center axis of the syringe barrel and a center axis of the plunger are not in a state of coinciding with each other, the screw portion at the tip of the plunger cannot be smoothly screwed into the rear face of the gasket. However, it is not easy to make the center axis of the syringe barrel and the center axis of the plunger coincide with each other and the screw portion at the tip of the plunger is sometimes forced to be screwed into the rear face of the gasket in a state in which both of the center axes deviate from each other.

However, if the gasket is mounted on the screw portion at the tip of the plunger in the state in which the center axis of the syringe barrel and the center axis of the plunger deviate from each other, the gasket at the tip of the plunger becomes in a skewed position (a position in which the center axis of the gasket deviates from the center axis of the plunger) and the gasket becomes unable to smoothly move in the syringe barrel, which causes a problem that performance in filling the liquid medicine deteriorates. In addition, as a result of the gasket being in the skewed position, clearance is made between an inner surface of the syringe barrel and an outer circumferential surface of the gasket and fluid leakage easily occurs from the clearance.

It is an object of the present invention to provide a plunger for a syringe in which a gasket can be mounted on a screw portion at a tip of the plunger in a state in which a center axis of a syringe barrel and a center axis of the plunger are easily made to coincide with each other.

DISCLOSURE OF THE INVENTION

In order to achieve the object, disclosed in claim 1 is a plunger for a syringe used for supporting and moving a gasket inserted in a syringe barrel, which is characterized in that it comprises: a screw portion formed at a tip thereof for mounting the gasket; a pair of ring members arranged at an interval from each other at the rear of the screw portion around a center axis of the plunger; and a plurality of vane members arranged radially from the center axis of the plunger between the ring members, and that outer diameters of the ring members and the vane members are equal to an inner diameter of the syringe barrel or slightly smaller than the inner diameter.

In the plunger according to claim 1, the interval between the pair of ring members arranged at the rear of the screw portion is preferably, for example, 0.5 mm or larger. As for the plunger according to claim 1, when the syringe is used, the plunger is inserted from a rear end of the syringe barrel and outer circumferential surfaces of the pair of ring members arranged at the interval from each other at the rear of the screw portion and outer circumferential surfaces of the vane members abut on an inner surface of the syringe barrel to guide the plunger, which indicates that a center axis of the syringe barrel and the center axis of the plunger naturally become in a state of coinciding with each other when the plunger is inserted from the rear end of the syringe barrel. Therefore, using the plunger according to claim 1, the center axis of the syringe barrel and the center axis of the plunger are made to coincide with each other easily without precise positioning, which makes it possible to mount the gasket at the tip of the plunger in a correct state (a position in which a center axis of the gasket coincides with the center axis of the plunger). As a result, the gasket can move smoothly in the syringe barrel, which prevents deterioration of performance in filling a liquid medicine and fluid leakage from a part between the inner surface of the syringe barrel and the outer circumferential surface of the gasket.

In the plunger according to claim 1, it is also suitable that the liquid medicine is previously filled in the syringe barrel as described in claim 2. Further, as described in claim 3, eight pieces of the vane members are arranged, for example, at regular intervals and at central angles of 45°.

In addition, as described in claim 4, it is also suitable that the plunger further comprises a flange portion formed at a rear end of the plunger; and one or two or more gripping ring members arranged near the front of the flange portion around the center axis of the plunger, and that outer diameters of the gripping ring members are equal to the inner diameter of the syringe barrel or slightly smaller than the inner diameter. Disclosed in claim 5 is a plunger for a syringe used for supporting and moving a gasket inserted in a syringe barrel, which is characterized in that it comprises: a screw portion formed at a tip thereof for mounting the gasket; a flange portion formed at a rear end thereof; and one or two or more gripping ring members arranged near the front of the flange portion around a center axis of the plunger, and that outer diameters of the gripping ring members are equal to an inner diameter of the syringe barrel or slightly smaller than the inner diameter.

As for the plunger according to claims 4 and 5, when the plunger is inserted from a rear end of the syringe barrel, the gripping ring members can be gripped so that the tip of the plunger can be easily inserted.

BEST MODE FOR CARRYING OUT THE INVENTION

A preferred embodiment of the present invention will be explained below with reference to the drawings.

Figure 1:
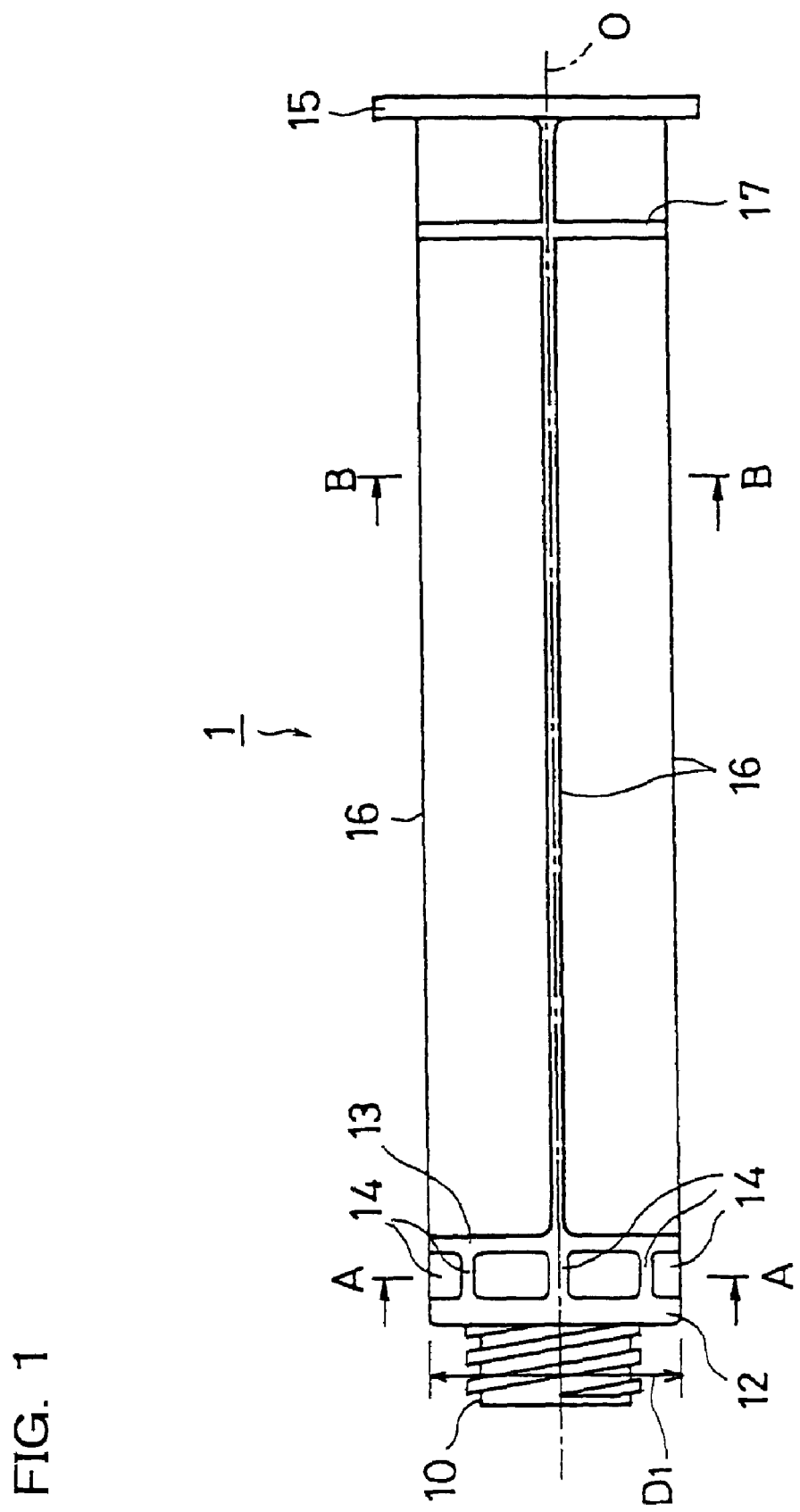
FIG. 1 is a side view of a plunger according to an embodiment of the present invention.
Figure 2:
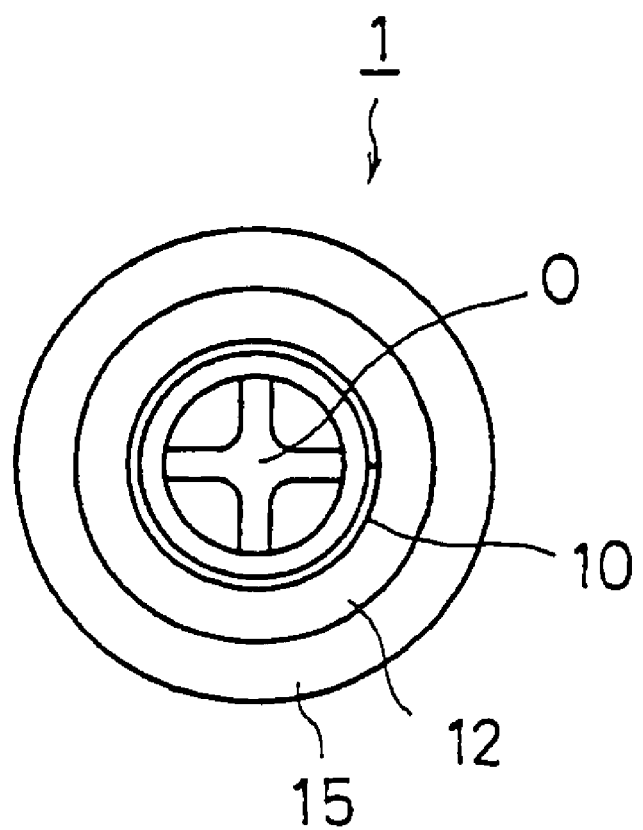
FIG. 2 is a front view of the plunger seen from a tip of the plunger.

At a tip of a plunger 1, a screw portion 10 for mounting a gasket 25 provided in a later-described syringe 2 is formed. At the rear of the screw portion 10 (the right in FIG. 1), a pair of ring members 12 and 13 are arranged at an interval from each other and a plurality of vane members 14 are arranged between the ring members 12 and 13. One of the ring members 12 is arranged in contact with the screw portion 10 at the tip of the plunger 1 while the other one of the ring members 13 is arranged at the rear of the one of the ring members 12 at the interval therebetween, and the interval between the ring members 12 and 13 is 0.5 mm or larger.

Each of the ring members 12 and 13 has a discoidal shape around a center axis O of the plunger 1. Diameters D1 of the ring members 12 and 13 are equal to an inner diameter D of a syringe barrel 20 of a later-described syringe 2 or slightly smaller than the inner diameter D of the syringe barrel 20.

Figure 3:
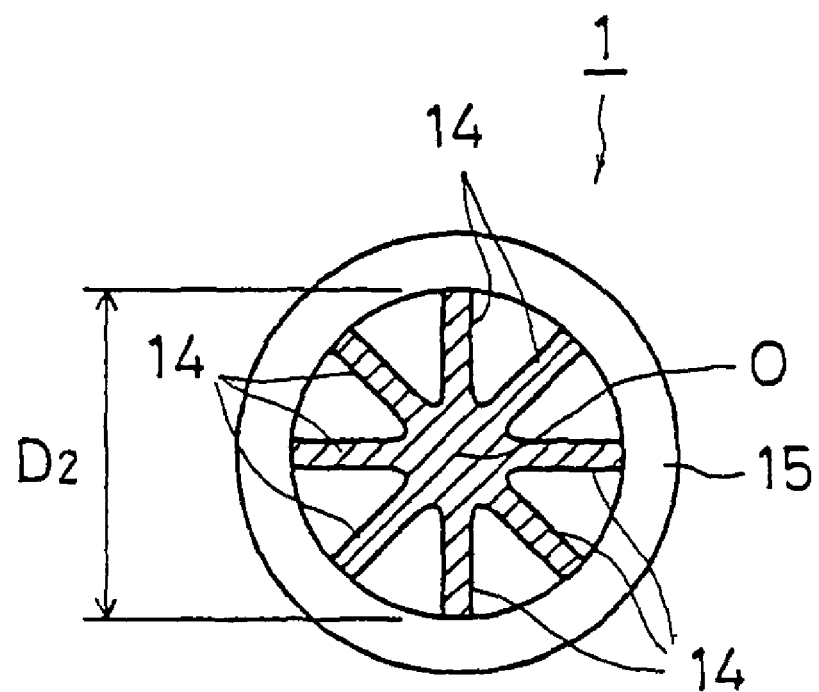
FIG. 3 is a cross-sectional view taken along the A-A line in FIG. 1.

In this embodiment, eight pieces of the vane members 14 are arranged between the ring members 12 and 13. As shown in FIG. 3, the vane members 14 are arranged radially from the center axis O of the plunger 1 and the vane members 14 are arranged around the center axis O of the plunger 1 at regular intervals and at central angles of 45°. An outer diameter D2 of the vane members 14 is also equal to the inner diameter D of the syringe barrel 20 of the later-described syringe 2 or slightly smaller than the inner diameter D of the syringe barrel 20.

Figure 4:
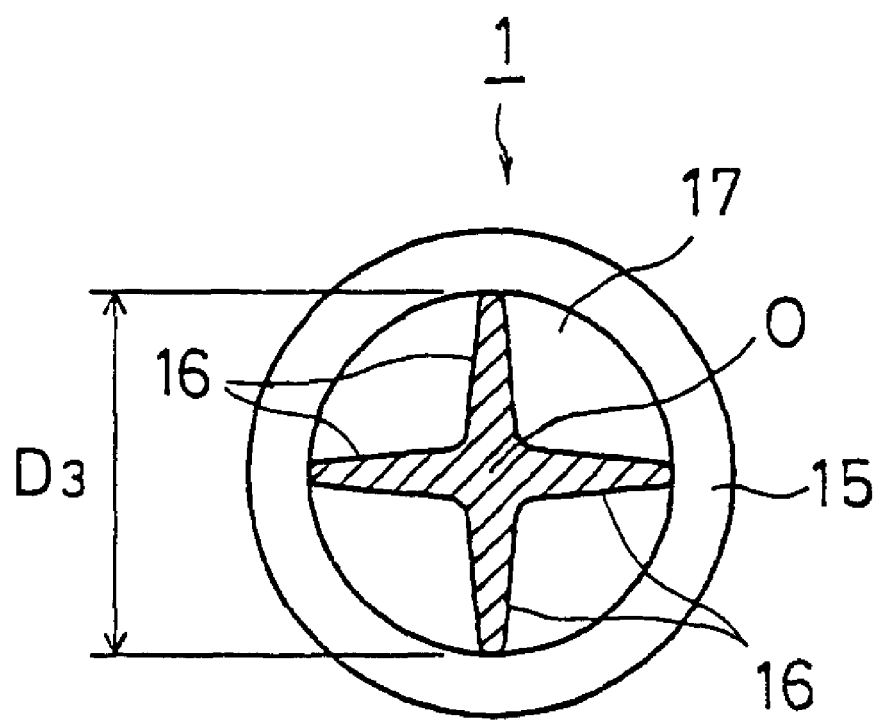
FIG. 4 is a cross-sectional view taken along the B-B line in FIG. 1.

At a rear end of the plunger 1 (the right end in FIG. 1), a flange 15 is formed. Further, between the flange 15 and the ring member 13, a rib 16 whose cross-sectional shape is a shape of a cross as shown in FIG. 4 is provided. Furthermore, a gripping ring member 17 is arranged near the front (near the left in FIG. 1) of the flange portion 15 at the rear end of the plunger 1. The gripping ring member 17 has also a discoidal shape around the center axis O of the plunger 1. In addition, a diameter D3 of the gripping ring member 17 is also equal to the inner diameter D of the syringe barrel 20 of the later-described syringe 2 or slightly smaller than the inner diameter D of the syringe barrel 20. The plunger 1 as described above can be integrally molded of plastic such as, for example, polypropylene.

Figure 5:
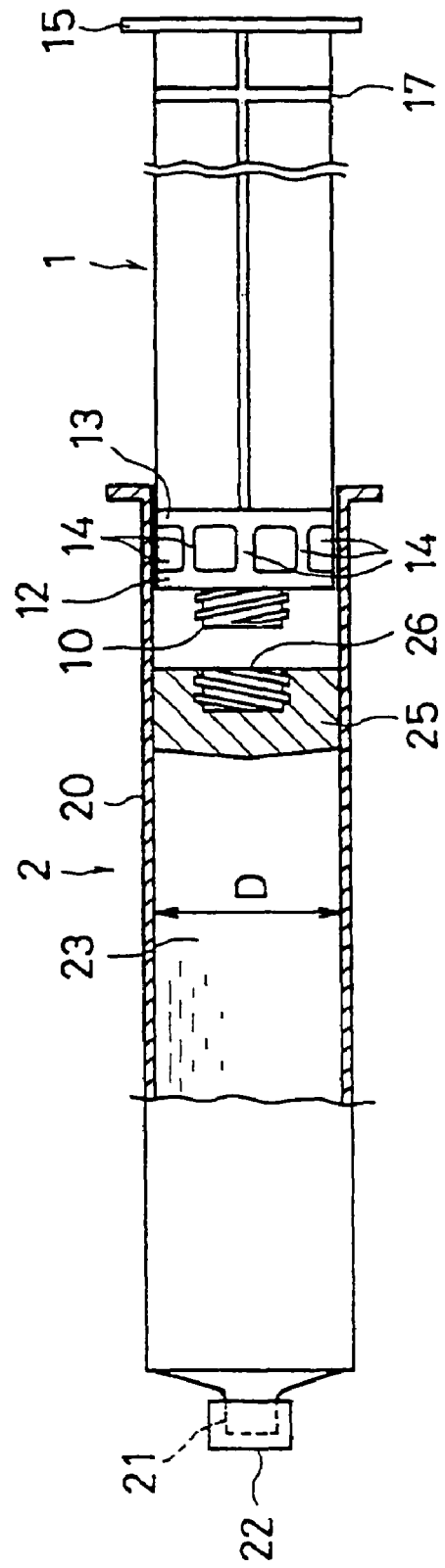
FIG. 5 is an explanatory view in a state in which the plunger according to the embodiment of the present invention is inserted in a syringe.

As shown in FIG. 5, in the syringe 2, at a tip (the left end in FIG. 5) of the syringe barrel 20 which has a cylindrical shape, a lure lock portion 21 is provided, and the lure lock portion 21 is in a state of being covered by a cap 22 before the syringe 2 is used. The inner diameter D of the syringe barrel 20 is equal to the diameters D1 of the ring members 12 and 13, the diameter D3 of the gripping ring member 17, and the outer diameter D2 of the vane members 14 explained above, or slightly larger than the diameters D1 of the ring members 12 and 13, the diameter D3 of the gripping ring member 17, and the outer diameter D2 of the vane members 14. Material of the above-described syringe barrel 2 is plastic such as a cyclic polyolefin resin, for example.

In the syringe barrel 20, liquid 23 such as, for example, a contrast medium is filled. Further, a gasket 25 having a substantially columnar shape is inserted in the syringe barrel 20 from an open rear end (the right end in FIG. 5) of the syringe barrel 20, and by the insertion of the gasket 25 in the syringe barrel 20, the liquid 23 is in a state of being sealed in the syringe barrel 20. An outer circumferential surface of the gasket 25 is in close contact with an inner surface of the syringe barrel 20, and thereby, the liquid 23 is not leaked from a part between the outer circumferential surface of the gasket 25 and the inner surface of the syringe barrel 20. In a rear face of the gasket 25 (the right end face in FIG. 5), a screw hole 26 into which the screw portion 10 formed at the tip of the aforesaid plunger 1 is screwed is formed.

Here, when the syringe 2 is used, the tip of the plunger 1 according to the embodiment of the present invention is first inserted from the rear end of the syringe barrel 20. In this case, in the plunger 1 of the embodiment, since the gripping ring member 17 is arranged near the front of the flange portion 15 at the rear end of the plunger 1, the gripping ring member 17 can be gripped when the plunger 1 is thus inserted from the rear end of the syringe barrel 1 and the plunger 1 can be easily inserted.

When the tip of the plunger 1 is inserted from the rear end of the syringe barrel 20 in this way, as shown in FIG. 5, outer circumferential surfaces of the ring members 12 and 13 and outer circumferential surfaces of the vane members 14 abut on the inner surface of the syringe barrel 20 to guide the plunger 1 so that the center axis O of the plunger 1 naturally becomes in a state in which it coincides with a center axis of the syringe barrel 20. In the state in which the center axis O of the plunger 1 coincides with the center axis of the syringe barrel 20, the plunger 1 is pushed straight into the syringe barrel 20 and the plunger 1 is further turned to screw the screw portion 10 at the tip of the plunger 1 into the screw hole 26 on the rear face of the gasket 25 so that the gasket 25 can be mounted at the tip of the plunger 1 in a correct position (a position in which the center axis of the gasket 25 is made to coincide with the center axis of the plunger 1) as shown in FIG. 6.

Figure 6:
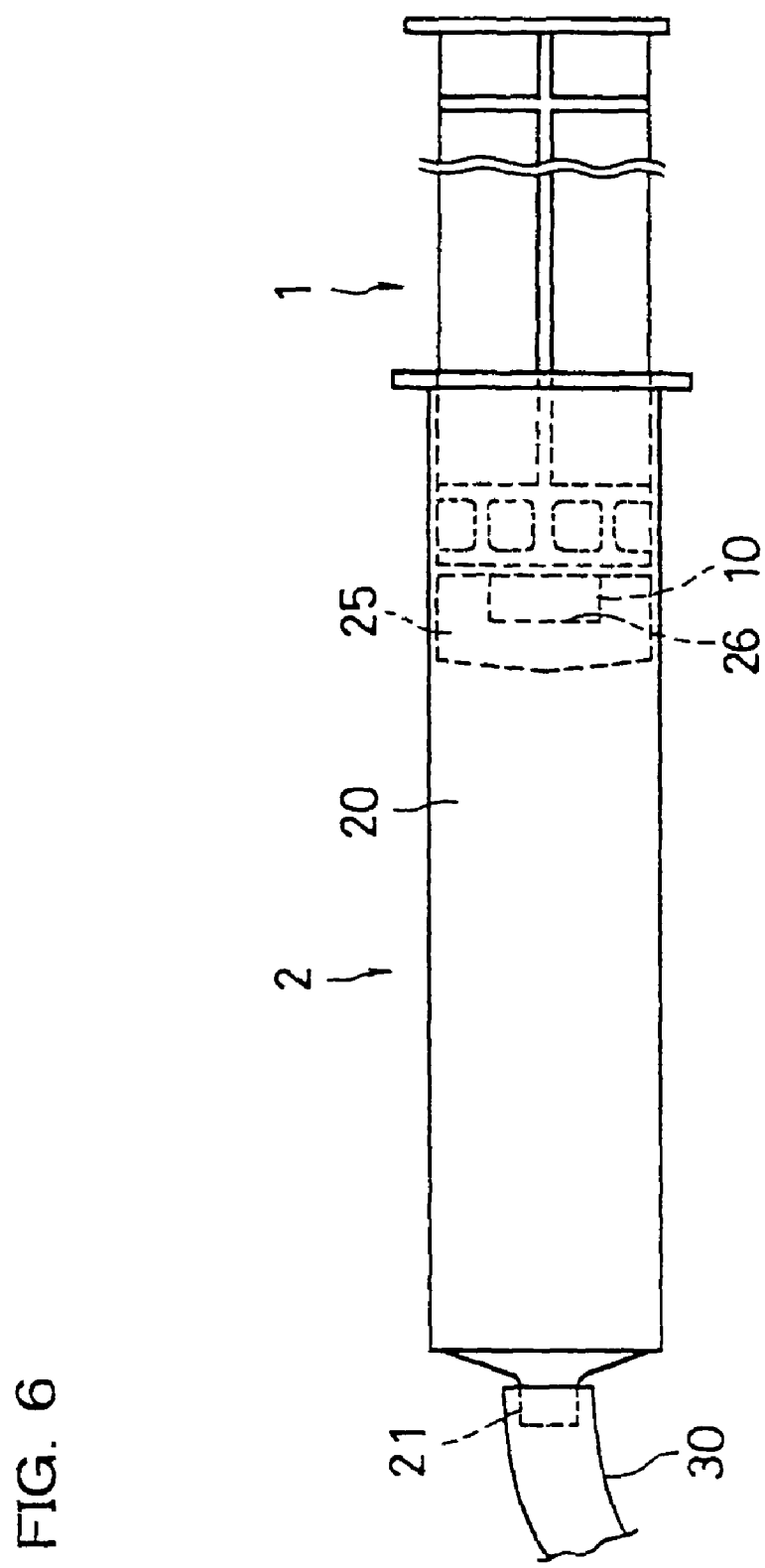
FIG. 6 is an explanatory view in a state in which a gasket is mounted on the tip of the plunger.

On the other hand, as shown in FIG. 6, an end of an extension tube 30, for example, is set at the lure lock portion 21 at the tip of syringe barrel 20. The gasket 25 is then pushed via the plunger 1 and thereby the liquid medicine 23 can be injected into an intended position in a body or the like through the extension tube 30.

Although an example in which only one of the gripping ring member 17 is provided near the front of the flange portion 15 at the rear end of the plunger 1 is explained in the embodiment shown in the drawings, two or more of the gripping ring members 17 may be provided near the front of the flange portion 15. Incidentally, an example of the plunger 1 in which the pair of ring members 12 and 13 and the gripping ring member 17 are formed around the center axis O of the plunger 1 and the vane members 14 are arranged radially from the center axis O of the plunger 1 is explained above, but it can be also considered that the whole plunger is formed in a round rod shape having a diameter equal to the inner diameter D of the syringe barrel 20 or slightly smaller than the inner diameter D instead of providing the aforesaid ring members 12, 13, and 17 and vane members 14. If the whole plunger is so formed in the round rod shape, however, a so-called dimensional shrink is caused in dimensional finishing when molded, which makes it difficult to obtain a plunger of accurate size. Accordingly, if the plunger is structured to have the ring members 12, 13, and 17 and the vane members 14, as the plunger 1 explained in the embodiment of the present invention, such a dimensional shrink can be prevented and the plunger 1 of accurate size can be obtained.

INDUSTRIAL AVAILABILITY

According to claims 1 to 4, it becomes possible to make a center axis of a syringe barrel and a center axis of a plunger coincide with each other easily without precise positioning so that a gasket can be mounted at a tip of the plunger in a correct position in which a center axis of the gasket coincides with the center axis of the plunger. Therefore, when the syringe is used, the gasket can move in the syringe barrel smoothly, which prevents deterioration of performance in filling a liquid medicine and fluid leakage from a part between an inner surface of the syringe barrel and an outer circumferential surface of the gasket. Further, according to claims 4 and 5, when the plunger is inserted from a rear end of the syringe barrel, a gripping ring member can be gripped so that the tip of the plunger can be easily inserted.

EXPLANATION OF CODES

1 plunger
2 syringe
10 screw portion
12, 13 ring member
14 vane member
15 flange
16 rib
17 ring member
20 syringe barrel
21 lure lock portion
22 cap
23 liquid
25 gasket
26 screw hole
30 extension tube

The invention claimed is:

1. A method for mounting a gasket inserted in a syringe barrel previously filled with a liquid medicine onto a plunger screw portion of a plunger at a tip thereof, the plunger including the plunger screw portion having a plunger spiral groove formed at a tip thereof for mounting the gasket, a pair of ring members arranged disposed apart from one another at an interval at a rear of the plunger screw portion around a center axis of the plunger and a plurality of vane members arranged radially from the center axis of the plunger between the ring members, outer diameters of the ring members and the vane members are equal, the pair of ring members arranged in a region of the plunger so that when the tip of the plunger is inserted from a rear end of a syringe barrel before the plunger screw portion is connected to a gasket screw portion having a gasket spiral groove of the gasket, outer circumferential surfaces of the ring members and the vane members abut on an inner surface of the syringe barrel to guide the plunger, the outer diameters of the ring members and the vane members being equal to an inner diameter of the syringe barrel or slightly smaller than the inner diameter, the method comprising the steps of:

inserting the gasket into syringe barrel with the gasket screw portion facing outwardly of the syringe barrel;

then inserting the plunger into the syringe barrel such that the plunger screw portion and the gasket screw portion are facially opposed to each other; and, inserting the plunger screw portion into the gasket screw portion and rotating the plunger until the gasket and the plunger are rotatably connected together, wherein the center axis of the plunger extends centrally through the plunger screw portion, the gasket, the gasket screw portion and the syringe barrel, wherein a liquid medicine is previously filled in the syringe barrel.

2. A method according to claim 1, wherein the plunger includes a plurality of ribs, the plurality of ribs extending longitudinally between and being connected to one of the ring members and the flange portion.

* * * * *